United States Patent [19]

Fujishima et al.

[11] Patent Number: 4,746,611
[45] Date of Patent: May 24, 1988

[54] PROCESS FOR RECOVERING CELLULASES

[75] Inventors: Shizu Fujishima, Ikeda; Fumiko Yaku, Suita; Einosuke Muraki, Osaka, all of Japan

[73] Assignee: Agency of Industrial Science & Technology, Tokyo, Japan

[21] Appl. No.: 814,478

[22] Filed: Dec. 30, 1985

[30] Foreign Application Priority Data

Jan. 10, 1985 [JP] Japan .................................. 60-3055
Jan. 22, 1985 [JP] Japan ................................ 60-10223

[51] Int. Cl.$^4$ ........................... C12N 9/42; C12R 1/66
[52] U.S. Cl. ................................... 435/209; 435/813; 435/913
[58] Field of Search ........................ 435/209, 99, 813

[56] References Cited

U.S. PATENT DOCUMENTS

| | | | |
|---|---|---|---|
| 4,167,447 | 9/1979 | Masri et al. | 435/178 |
| 4,510,248 | 4/1985 | Nakanishi et al. | 435/226 |
| 4,552,845 | 11/1985 | Reid | 435/206 |

OTHER PUBLICATIONS

Bungay in Enzyme Engineering 7, (N.Y. Academy of Sciences), 1984, pp. 155–157.
Sinitsyn et al. in Applied Biochemistry and Biotechnology, vol. 8, pp. 25–29, (1983).

*Primary Examiner*—Lionel M. Shapiro
*Attorney, Agent, or Firm*—Armstrong, Nikaido, Marmelstein & Kubovcik

[57] ABSTRACT

A cellulosic material is saccharified by cellulases and the resulting saccharified solution is acidified. Subsequently chitosan and/or partially deacetylated chitin are dissolved therein and the obtained solution is alkalified. Thus the cellulases are absorbed by the chitosan and/or partially deacetylated chitin. Further a cellulosic material is saccharified by at least one cellulase originating from a fungus belonging to the genus Aspergillus and at least either chitosan and/or partially deacetylated chitin are added to the resulting saccharified solution to thereby adsorb the cellulase by the chitosan and/or partially deacetylated chitin.

21 Claims, No Drawings

PROCESS FOR RECOVERING CELLULASES

BACKGROUND OF THE INVENTION

This invention relates to a process for recovering cellulases. More particularly, it relates to a process for efficiently recovering cellulases wherein a cellulosic material is saccharified by decomposition with cellulases and the residual cellulases are recovered from the resulting saccharified solution in a quite simplified manner.

Recent problems such as energy and food crises and environmental pollution have brought about many studies for effectively utilizing undeveloped resources including those on the saccharification of cellulosic materials.

In particular, enzymatic saccharification has attracted a wide attention since it can be performed in a convenient manner with simple equipment under mild conditions and sugars thus obtained would not further decompose.

However, the expense for the production of enzymes such as cellulases and hemicellulases generally amounts to nearly a half of the total cost of the enzymatic saccharification. Therefore it is very important to recover and reuse expensive enzymes.

Thus, it has been proposed to recover cellulases from a saccharified solution by, for example, ultrafiltration or precipitation with organic solvents.

However, ultrafiltration is very expensive since it must be carried out under an elevated pressure. On the other hand, precipitation with organic solvents is not preferable from the viewpoint of the cost of solvents and the recovery. In addition, each procedure has a disadvantage such that enzymes are highly likely to be inactivated during the treatment.

On the other hand, there has been known a process for accelerating the saccharification of a cellulosic material with a combined use of cellulases originating from fungi belonging to the genera Trichoderma and Aspergillus. However, it is then unavoidable that the yield of the cellulase originating from fungi belonging to the genus Aspergillus is significantly lower than that of the one originating from the genus Trichoderma since the affinity of the former cellulase for the cellulosic material is much lower than that of the latter.

SUMMARY OF THE INVENTION

It is a first object of the present invention to provide a process for economically and efficiently recovering residual cellulases from a saccharified solution obtained by saccharifying a cellulosic material with the cellulases in a quite simplified manner.

It is a second object of the present invention to provide a process for recovering in high yields residual cellulases in a saccharified solution obtained by saccharifying a cellulosic material with the cellulases.

It is a third object of the present invention to provide a process for recovering cellulases from a saccharified solution obtained by saccharifying a cellulosic material with the cellulases while minimizing inactivation of the enzymes.

DETAILED DESCRIPTION OF THE PREFERRED EMBODIMENTS

The present invention has been completed based on the following findings:

A. Chitosan and partially deacetylated chitin both derived from chitin which widely occurs in nature are highly soluble in an acidic aqueous solution but insoluble in a neutral or basic aqueous solution and show excellent affinities for protein.

B. Chitosan and partially deacetylated chitin show particularly high affinities for cellulases originating from fungi belonging to the genus Aspergillus.

That is, a first aspect of the present invention, which has been completed based on the above finding A, comprises acidifying a saccharified solution obtained by saccharifying a cellulosic material with cellulases; adding chitosan and/or partially deacetylated chitin to the saccharified solution to thereby dissolve them therein; alkalifying the obtained mixture to thereby precipitate cellulases adsorbed by the chitosan and/or partially deacetylated chitin; and separating the precipitate to thereby recover cellulases.

On the other hand, a second aspect of the present invention, which has been completed based on the above finding B, comprises adding at least chitosan and/or partially deacetylated chitin to a saccharified solution obtained by saccharifying a cellulosic material with at least one of cellulases originating from a fungus belonging to the genus Aspergillus; selectively adsorbing the cellulases originating from the fungus belonging to the genus Aspergillus by said additives; and separating the same to thereby recover cellulases.

(1) Now the first aspect of the present invention will be described in detail. Examples of the cellulosic material as used herein are any wood material such as small wood chips, sawdust, cortex and wood waste matters obtained from conifers, broadleaf trees, Southeast Asian and Far Eastern woods, agricultural wastes requiring a disposal cost such as rice straws and those obtained from cane or corn; and paper such as newspapers and corrugated cardboard.

The cellulases as used herein may be derived from any source. For example, enzymes including cellulases and hemicellulases originating from fungi belonging to the genera Trichoderma and Aspergillus may be employed.

One of these enzymes having its inherent origin may be used alone. Alternatively, two or more enzymes may be used at the same time. It is also possible to employ a cell extract or a culturing broth containing these enzymes as an enzyme source.

The first aspect of the present invention is characterized in that chitosan and/or partially deacetylated chitin are used as adsorbent for cellulases and that the chitosan and/or partially deacetylated chitin are dissolved for use in the adsorption of the cellulases.

Chitosan, which is a polysaccharide comprising $\beta$-1, 4 bonds consisting of D-glucosamine as a basic unit, is obtained by deacetylating chitin, which is a constituent of shells of crustaceans such as lobsters and crabs by repeatedly heating with 40 to 50% by weight of an alkaline aqueous solution of 60° C. or above. On the other hand, deacetylated chitin is a partially deacetylated intermediate obtained during the preparation of the above chitosan and contains acetyl groups in an amount less than 10% of chitin.

These chitosan and partially deacetylated chitin have excellent affinities for protein and are available, in particular, as adsorbents for cellulases.

As described above, these chitosan and partially deacetylated chitin are soluble in an acidic aqueous solution but insoluble in a neutral or basic aqueous solution.

In the first aspect of the present invention, either the chitosan or the partially deacetylated chitin may be employed alone. Alternatively, it is also possible to use both together.

The ability of chitosan to adsorb cellulases is practically similar to that of partially deacetylated chitin so that an appropriate amount of each material may be selected when they are simultaneously employed.

In the first aspect of the present invention, a saccharified solution obtained by saccharifying a cellulosic material with cellulases is acidified and chitosan and/or partially deacetylated chitin are added thereto and dissolved therein in order to recover the residual cellulases from the saccharified solution.

The condition under which the cellulosic material is saccharified is not strictly limited. For example, the cellulosic material is ground and added to a buffer solution, e.g., an acetate buffer solution. Then cellulases are added thereto and the mixture is shaken at 10° to 60° C. for several hours to several days. The chitosan and/or partially deacetylated chitin may be dissolved in the saccharified solution after acidifying the saccharified solution while it still contains unreacted cellulosic material. Alternatively, the chitosan and/or partially deacetylated chitin may be added to the saccharified solution after separating unreacted cellulosic material therefrom by, e.g., filtration or centrifugation followed by acidification of the same.

An acid is added to the saccharified solution or the filtrate obtained by removing unreacted matters therefrom in such an amount as to dissolve the chitosan and/or partially deacetylated chitin without causing denaturation of the constituents nor inactivation of enzymes, thus adjusting the solution to a pH value usually ranging from 2.3 to 6.8.

However, saccharification of a cellulosic material with cellulases is generally performed under an acidic condition because of the stability of the enzymes, so that it is usually unnecessary to further add an acid.

When, however, the molecular weight of the chitosan makes it difficult to rapidly decompose the same, when a difference in the degree of deacetylation makes it difficult to decompose the partially deacetylated chitin or when a buffer solution in which the additives are hardly soluble is employed, it is preferable to add a monobasic acid such as acetic acid or hydrochloric acid thereto in an amount at least equivalent to the amino groups in the employed chitosan and/or partially deacetylated chitin.

The chitosan and/or partially deacetylated chitin are added in an amount of one to 15 times, preferably two to five times as much as that of the residual cellulases.

After adding the chitosan and/or partially deacetylated chitin, the mixture is allowed to stand for 30 min to several hours depending on the molecular weight of the chitosan or the degree of acetylation of the partially deacetylated chitin as described above to thereby dissolve the additives in the saccharified solution previously acidified.

Subsequently the saccharified solution in which the chitosan and/or partially deacetylated chitin are dissolved or the filtrate obtained therefrom is alkalified to give a pH value ranging from 7.0 to 10, thus precipitating the cellulases adsorbed by the chitosan and/or partially deacetylated chitin for ten to several tens min. 1 to 15% of ethanol may be added to accelerate the precipitation.

The alkali used in the above alkalification is not strictly limited. Preferable examples thereof are sodium hydroxide and potassium hydroxide. Then the precipitated cellulases adsorbed by the chitosan and/or partially deacetylated chitin are separated by, e.g., filtration or centrifugation.

When the chitosan and/or partially deacetylated chitin are added to the saccharified solution without removing unreacted cellulosic material, the cellulases adsorbed by the chitosan and/or partially deacetylated chitin are separated together with the unreacted cellulosic material.

The abovementioned pH adjustment and dissolution and precipitation of the chitosan and/or partially deacetylated chitin may be carried out at 10° to 60° C., usually at room temperature.

According to the first aspect of the present invention as described above, 90 to 95% of the residual cellulases in the saccharified solution or filtrate can be recovered. It is further possible that the saccharified solution is separated into unreacted cellulosic material and a filtrate; the residual cellulases in the unreacted cellulosic material are eluted in a conventional manner with the use of, e.g., ethylene glycol, a pH buffer solution, a surfactant or urea if necessary; the obtained eluate is added to the above filtrate; and the cellulases are recovered from the resulting mixture according to the first aspect of the present invention.

Furthermore, the cellulases adsorbed by the chitosan and/or partially deacetylated chitin separated according to the first aspect of the present invention are optionally mixed with the unreacted cellulosic materials and the resulting mixture is added to an aqueous solution or a buffer solution of a pH value of 2.3 to 6.8 containing a fresh substrate. Fresh cellulases are further added thereto if necessary, thus further saccharifying the cellulosic material.

Thus, when the chitosan and/or partially deacetylated chitin have been already added to the saccharified solution, the residual cellulases in the saccharified solution can be recovered in the same manner as described above without adding fresh chitosan and/or partially deacetylated chitin.

That is, the first aspect of the present invention makes it possible to repeatedly use the chitosan and/or partially deacetylated chitin.

According to the first aspect of the present invention, it is possible to recover the cellulases in a quite simplified manner by merely adjusting the pH value of the saccharified solution and using the chitosan and/or partially deacetylated chitin as described above. Therefore, the cost of the saccharification of the cellulosic material can be remarkably lowered in this manner.

(2) Now the second aspect of the present invention will be described. The cellulosic material to be used in the second aspect of the present invention is completely the same as that used in the first aspect. The enzyme to be used in the second aspect comprises at least one of cellulases originating from a fungus belonging to the genus Aspergillus. For example, a cellulase originating from a fungus belonging to the genus Aspergillus may be employed alone. Alternatively, a mixture of cellulases originating from a fungus belonging to the genus Aspergillus and those originating from a fungus belonging to the genus Trichoderma may be used. These enzymes may include hemicellulases. In addition, a cellular extract or a culturing broth containing these enzymes may be used as the enzyme source.

The second aspect of the present invention is characterized in that cellulases originating from a fungus belonging to the genus Aspergillus are selectively adsorbed by chitosan and/or partially deacetylated chitin.

The chitosan and/or partially deacetylated chitin to be employed in the second aspect include those described in the first aspect of the present invention. However, it is preferable that the chitosan is cross-linked and that the deacetylated chitin contains acetyl groups in an amount more than 10% in order to lower the solubility under an acidic condition. The cross-linked chitosan and partially deacetylated chitin containing more than 10% of acetyl groups can exhibit excellent affinities for cellulases originating from fungi belonging to the genus Aspergillus.

That is, in the second aspect of the present invention, at least either chitosan and/or partially deacetylated chitin are added to a saccharified solution obtained by saccharifying a cellulosic material with cellulases comprising at least one of cellulases originating from a fungus belonging to the genus Aspergillus and the residual cellulases originating from a fungus belonging to the genus Aspergillus in the saccharified solution are predominantly adsorbed by the chitosan and/or partially deacetylated chitin.

The saccharified solution may contain unreacted cellulosic material. Alternatively, a filtrate obtained by removing the unreacted cellulosic material from the saccharified solution by, e.g., filtration or centrifugation may be used.

The chitosan and partially deacetylated chitin may be added separately. Alternatively, a mixture thereof may be added.

Furthermore, the chitosan and/or partially deacetylated chitin may be added simultaneously with a fresh substrate.

The chitosan and/or partially deacetylated chitin are added in an amount one to 15 times, preferably two to five times, as much as the amount of the cellulases originating from a fungus belonging to the genus Aspergillus which are used in the saccharification.

In the second aspect of the present invention, the addition of the chitosan and/or partially deacetylated chitin, the adsorption of the cellulases and the separation of the same are performed at 10° to 60° C. Usually it is preferable to perform these procedures at room temperature from an economical viewpoint. The chitosan and/or partially deacetylated chitin are added to the saccharified solution of a pH value ranging from 4.0 to 10.0. When the pH value of the saccharified solution is less than 4.0, the chitosan and/or partially deacetylated chitin are dissolved therein. When it exceeds 10.0, undesirable denaturation of the cellulases may occur.

The adsorption of the cellulases by the chitosan and/or partially deacetylated chitin requires a shorter period, i.e. usually ten to 30 min, compared with that in the first aspect of the present invention. In the case of chitin of such a molecular weight or partially deacetylated chitin of such a degree of acetylation as to bring about a high solubility, it is desirable to complete the adsorption within 30 min, although a decrease by 10 to 30% in the degree of adsorption may occur.

When chitosan and/or partially deacetylated chitin are exclusively added to a saccharified solution obtained by saccharifying a cellulose material with a cellulase originating from a fungus belonging to the genus Aspergillus and a one originating from a fungus belonging to the genus Trichoderma, only the former cellulase is adsorbed in an amount of 50 to 70% of the residual cellulase. On the other hand, when chitosan and/or deacetylated chitin are added simultaneously with a fresh substrate, 90 to 100% of the residual cellulase originating from the fungus belonging to the genus Trichoderma and 60 to 80% of the residual cellulase originating from the fungus belonging to the genus Aspergillus in the saccharified solution are adsorbed.

When chitosan and/or partially deacetylated chitin are exclusively added to a saccharified solution obtained by saccharifying a cellulose material with a cellulase originating from a fungus belonging to the genus Aspergillus alone, 50 to 70% of the residual cellulase was adsorbed. On the other hand, when chitosan and/or partially deacetylated chitin are added to a saccharified solution with a fresh substrate, 60 to 80% by weight of the cellulase is adsorbed.

After adsorbing cellulases by the chitosan and/or partially deacetylated chitin as described above, the cellulases adsorbed by the chitosan and/or partially deacetylated chitin are separated by, e.g., centrifugation. When a fresh substrate is added in the adsorption, the cellulases adsorbed by the chitosan and/or partially deacetylated chitin thus obtained are suspended in an aqueous solution or an acetate or citrate buffer solution of a pH value ranging from 3.0 to 6.8 as such and fresh cellulases are added thereto, if necessary, followed by the reuse of the cellulases adsorbed by the chitosan and/or partially deacetylated chitin in saccharification in a conventional manner.

When no fresh substrate is added in the adsorption, the cellulases adsorbed by the chitosan and/or partially deacetylated chitin are filtered and added to a buffer solution and a fresh substrate and fresh cellulases are added thereto if necessary, followed by reuse of the cellulases adsorbed by the chitosan and/or partially deacetylated chitin in saccharification.

As described above, in the second aspect of the present invention, cellulases originating from the fungus belonging to the genus Aspergillus can be very readily recovered from a saccharified solution obtained by saccharifying a cellulosic material with cellulases comprising at least one of cellulases by the use of chitosan and/or partially deacetylated chitin having an excellent affinity for cellulases. Furthermore, other cellulases in addition to those originating from the fungus belonging to the genus Aspergillus may be very effectively recovered by using chitosan and/or partially deacetylated chitin simultaneously with a fresh substrate.

Thus, the second aspect of the present invention makes it possible to very effectively recover expensive cellulases in a convenient manner to thereby significantly lower the cost of saccharification similar to the first aspect of the present invention.

To further illustrate the present invention, the following Examples will be given.

EXAMPLE 1

4 g of a woodflour obtained by grinding Japanese red pine was added to 100 ml of an acetate buffer solution (pH 4.5) and 300 mg of a commercially available cellulase (Cellulase Onozuka R-10) originating from *Trichoderma viride* was further added thereto. The obtained mixture was shaken at 40° C. for 24 hours. When 48% of the woodflour was saccharified, the reacted solution was centrifuged and separated into a solution and unreacted solid matters. As a result of an analysis of the solution, it was found that there remained 60% of the cellulase.

Then, 400 mg of chitosan was added to the separated solution and dissolved therein by allowing to stand for two hours at room temperature. Then the solution was adjusted to a pH value of 9.0 with a 1 N aqueous solution of sodium hydroxide. Precipitation was completed after 30 min. Then the precipitate was filtered and dissolved in 60 ml of an acetate buffer solution (pH 4.5). The cellulase was determined to be 165 mg, suggesting that 92% of the same was recovered.

2.4 g of the woodflour of Japanese red pine was added to the solution of the precipitate and shaken at 40° C. for 24 hours. Thus 41% of the woodflour was saccharified.

The saccharified solution was adjusted to a pH value of 9.5 at room temperature as such. Precipitation was completed after 30 min. Then the precipitate was filtered with the unreacted residue and added to 60 ml of an acetate buffer solution (pH 4.5). 2.4 g of fresh woodflour of Japanese red pine was further added thereto and the mixture was allowed to react at 40° C. for 24 hours to give a degree of saccharification of 38%.

EXAMPLE 2

A bagasse from which lignin had been removed by treating with an alkali was ground to give a powder of ca. 20 mesh in size. 2 g of this powder was added to 50 ml of a citrate buffer solution (pH 4.0) and 200 mg of a cellulase (Cellulosine AP) originating from *Aspergillus niger* was further added thereto. The obtained mixture was shaken at 48° C. for 24 hours to give a degree of saccharification of 50%. Determination of the circular dichroism indicated that there remained 70% of the Cellulosine AP.

Then 380 mg of partially deacetylated chitin containing 5.6% of acetyl groups based on the chitin and 0.1 ml of glacial acetic acid were added to the solution and dissolved therein by allowing the mixture to stand for 1.5 hour. Then the obtained solution was adjusted to a pH value of 8.0 with a 0.1 N solution of sodium hydroxide and the precipitate thus formed was filtered after one hour. The filtrate contained a trace amount of the cellulase suggesting that most of the cellulase was removed with the partially deacetylated chitin.

EXAMPLE 3

100 ml of a water-soluble enriched medium containing an appropriate amount of a cellulose powder as a carbon source was introduced into a flask of 500 ml in volume and sterilized therein. Trichoderma viride QM 414 was inoculated thereto and cultured therein under an aerobic condition at 30° C. for six days. The pH value of the culturing broth was controlled to 5.4 throughout the culture.

3 g of a woodflour obtained by grinding Japanese beech was introduced into another flask of 100 ml in volume. 50 ml of the above culturing broth containing 120 mg of protein, i.e. the enzyme, was added thereto. After a reaction at 45° C. for 24 hours, a degree of saccharification of 40% was obtained. 58% of the initially added cellulase remained in the reaction mixture. Then it was separated into a solution and solid matters by centrifugation. 1.8 g of the solid matters were treated with 100 ml of water and 40 ml of an acetate buffer solution (pH 4.6) to thereby elute 40 mg of the residual cellulase containing 32 mg of protein from the solid matters. To the supernatant obtained by the above centrifugation, the combined eluates (140 ml in total) of the cellulase from the unreacted solid matters were added and 300 mg of chitosan was further added thereto and dissolved therein by allowing the mixture to stand for three hours at 30° C. Then the solution was adjusted to a pH value of 9.0 with an aqueous solution of sodium hydroxide.

After the completion of the precipitation, the precipitate was filtered and added to 40 ml of an acetate buffer solution (pH 4.9) to thereby dissolve therein. Then 1.2 g of a lauan powder was added to the obtained solution and saccharified therein at 45° C. for 48 hours to give a degree of saccharification of 45%.

EXAMPLE 4

75 mg of Cellulosine AP and 75 mg of Cellulase Onozuka R-10 were introduced into an Erlenmeyer flask of 100 ml in volume. 50 ml of a phosphate buffer solution (pH 4.5) was added thereto. 2 g of a sample obtained by powdering a dry newspaper was further added thereto and the mixture was shaken at 45° C. for 24 hours to give a degree of saccharification of 52%. To the solution, 350 mg of partially deacetylated chitin containing 8% of acetyl groups based on the chitin and 1.0 ml of 1 N HCl were added and the mixture was allowed to stand as such at room temperature for three hours to thereby dissolve the additives. Then the solution was adjusted to a pH value of 9.0 with 1 N NaOH. After one hour, the precipitate thus formed and the unreacted solid matters were filtered and added to an acetate buffer solution (pH 4.8). Additional 2 g of the above newspaper was added thereto and the mixture was shaken at 45° C. for 24 hours to give a degree of saccharification of 49%.

EXAMPLE 5

4 g of a woodflour obtained by grinding Japanese red pine was added to 100 ml of an acetate buffer solution (pH 4.5) and 150 mg portions of commercially available cellulases (Cellulase Onozuka R-10 and Cellulosine AP) originating from fungi belonging to the genera Trichoderma and Aspergillus respectively were added thereto. The reaction mixture was shaken at 40° C. for 24 hours. Then the saccharified solution wherein 60% of the woodflour was saccharified was centrifuged to separate solid matters. To the solution, 4 g of a woodflour of Japanese beech and 300 mg of a commercially available cross-linked chitosan were added and shaken. After one hour, the mixture was filtered and the solid matters thus obtained were suspended in an acetate buffer solution (pH 4.5) to thereby initiate the next reaction. After 24 hours, the degree of saccharification reached 40%. When the woodflour of Japanese beech was added without the chitosan, the degree of saccharification reached 23%.

EXAMPLE 6

2 g of a sample obtained by grinding a dry newspaper to give a powder of ca. 20 mesh in size was suspended in 50 ml of water and 100 mg of Cellulosine AP was added thereto. The saccharification of the newspaper was carried out at 45° C. for 24 hours to give a degree of saccharification of 35%. As a result of an analysis, it was found that 70% of the Cellulosine AP remained in the saccharified solution. 2 g of a woodflour of Japanese red pine and 500 mg of partially deacetylated chitin containing 19.0% of acetyl groups based on the chitin were added to the saccharified solution and the mixture was shaken at 40° C. for one hour. Then the Cellulosine in the saccharified solution decreased to 21%, suggesting that the 70% of the residual enzyme was adsorbed.

When the partially deacetylated chitin was added without the woodflour of Japanese red pine, 60% of the residual Cellulosine AP was adsorbed.

EXAMPLE 7

An appropriate amount of a cellulose powder was introduced into a flask of 500 cc in volume as a carbon source. 100 ml of a water-soluble enriched medium was added thereto and sterilized therein. Then *Trichoderma viride* QM 414 was inoculated thereto and cultured therein at 30° C. under an aerobic condition for six days. The pH value of the culturing broth was controlled to 5.4 throughout the culture.

2 g of a corn stem powder from which lignin was removed was introduced into another flask of 100 ml in volume. 500 ml of the above culturing broth containing 120 mg protein of the enzyme and 100 mg of a commercially available cellulase (Cellulosine AP) were added thereto and the saccharification was carried out at 40° C. for 24 hours to give a degree of saccharification of 60%. 2 g of a corn powder and 250 mg of chitosan insolubilized with epichlorohydrin were added thereto and the mixture was occasionally shaken at 30° C. for one hour. Then solid matters were separated and suspended in 50 ml of a citrate buffer solution (pH 5.0) to thereby initiate the next reaction at 40° C. The degree of saccharification after 24 hours reached 37%.

EXAMPLE 8

75 mg portions of Cellulase onozuka R-10 and Cellulosine AP and 2 g of a woodflour of Japanese red pine were introduced into a flask of 100 ml in volume and 50 ml of an acetate buffer solution (pH 4.5) was added thereto. After saccharifying for 24 hours, the mixture was separated into a solution and residual matters by centrifugation.

To the residual matters, 25 ml of a 5% aqueous solution of ethanol was added and the mixture was shaken at 40° C. for five hours to thereby elute 50% of the enzymes adsorbed by the residual matters. The solution thus recovered was added to the saccharified solution separated in the prior step. 3 g of a fresh woodflour of Japanese red pine and 600 mg of chitosan were added thereto and the mixture was shaken at room temperature for 20 min. Then solid matters were separated by centrifugation and suspended in 50 ml of an acetate buffer solution (pH 4.8). The saccharification was carried out at 45° C. for 24 hours. The degree of saccharification of the woodflour in this case was compared with that of another case wherein no chitosan was added. Thus it was found that the degree of saccharification of the former case was 1.5 times as high as that of the latter case.

EXAMPLE 9

A woodflour of Japanese red pine was saccharified in the same manner as described in Example 1. When the degree of saccharification reached to 55%, the reaction mixture was centrifuged to remove solid matters. To the obtained solution, 300 mg of a commercially available cross-linked chitosan was added and the mixture was shaken at 40° C. for one hour. Then the chitosan was filtered. The Cellulosine AP was exclusively adsorbed by the chitosan in a ratio of approximately 60% based on the residual Cellulosine AP in the solution from which the solid matters were separated.

We claim:

1. A process for recovering cellulases from a saccharified solution obtained by saccharifying a cellulosic material by using said cellulases, which comprises the steps of:
   (1) acidifying said saccharified solution,
   (2) adding chitosan and/or partially deacetylated chitin to said saccharified solution previously acidified in the preceding step and dissolving the same therein,
   (3) alkalifying the resulting solution to thereby precipitate said cellulases adsorbed by the chitosan and/or partially deacetylated chitin, and
   (4) separating the cellulases adsorbed by the chitosan and/or partially deacetylated chitin.

2. A process for recovering cellulases as set forth in claim 1, wherein said partially deacetylated chitin contains acetyl groups in an amount less than 10% of the chitin.

3. A process for recovering cellulases as set forth in claim 1, wherein said saccharified solution is acidified in the presence of unreacted cellulosic material.

4. A process for recovering cellulases as set forth in claim 1, wherein said saccharified solution is acidified after separating unreacted cellulosic material.

5. A process for recovering cellulases as set forth in claim 1, wherein said cellulases adsorbed by the chitosan and/or partially deacetylated chitin are separated together with the unreacted cellulosic material.

6. A process for recovering cellulases as set forth in claim 1, wherein said cellulases adsorbed by the chitosan and/or partially deacetylated chitin are exclusively separated.

7. A process for recovering cellulases as set forth in claim 1, wherein said acidification gives a pH value ranging from 2.3 to 6.8.

8. A process for recovering cellulases as set forth in claim 1, wherein said saccharified solution is acidified with acetic or hydrochloric acid.

9. A process for recovering cellulases as set forth in claim 1, wherein said chitosan and/or partially deacetylated chitin are added in an amount at least the same as that of the residual cellulases in the saccharified solution.

10. A process for recovering cellulases as set forth in claim 1, wherein the chitosan and/or partially deacetylated chitin is added to the saccharified solution previously acidified and the reaction mixture is allowed to stand or stirred for 30 min to several hours to thereby dissolve the same.

11. A process for recovering cellulases as set forth in claim 1, wherein said alkalification gives a pH value ranging from 7.0 to 10.

12. A process for selectively recovering from a saccharified solution cellulases originating from a fungus belonging to the genus Aspergillus, which comprises the steps of:
   (1) saccharifying a cellulose material by using at least one of cellulases originating from a fungus belonging to the genus Aspergillus,
   (2) adding at least either chitosan and/or partially deacetylated chitin to the saccharified solution to selectively adsorb said cellulases originating from the fungus belonging to the genus Aspergillus thereby, and (3) separating the cellulases originating from the fungus belonging to the genus Aspergillus adsorbed by the chitosan and/or partially deacetylated chitin.

13. A process for recovering cellulases as set forth in claim 12, wherein said chitosan is cross-linked.

14. A process for recovering cellulases as set forth in claim 12, wherein said partially deacetylated chitin contains acetyl groups in an amount more than 10% of the chitin.

15. A process for recovering cellulases as set forth in claim 12, wherein said chitosan and/or partially deacetylated chitin are added to said saccharified solution simultaneously with fresh substrates.

16. A process for recovering cellulases as set forth in claim 12, wherein at least either chitosan and/or partially deacetylated chitin are added to said saccharified solution in the presence of the unreacted cellulosic material.

17. A process for recovering cellulases as set forth in claim 12, wherein at least either chitosan and/or partially deacetylated chitin are added to said saccharified solution after removing the unreacted cellulosic material.

18. A process for recovering cellulases as set forth in claim 12, wherein said chitosan and/or partially deacetylated chitin are added in an amount at least the same as the residual cellulases in the saccharified solution.

19. A process for recovering cellulases as set forth in claim 12, wherein said saccharified solution has a pH value ranging from 4.0 to 10.0.

20. A process for selectively recovering from a saccharified solution cellulases originating from a fungus belonging to the genus Aspergillus, which comprises the steps of:
   (1) saccharifying a cellulose material by using a mixture of cellulases, at least one of said cellulases originating from a fungus belonging to the genus Aspergillus,
   (2) adding at least either chitosan and/or partially deacetylated chitin to the saccharified solution to selectively adsorb said cellulases originating from the fungus belonging to the genus Aspergillus thereby, and
   (3) separating the cellulases originating from the fungus belonging to the genus Aspergillus adsorbed by the chitosan and/or partially deacetylated chitin.

21. A process for recovering cellulases as set forth in claim 20, wherein in step (1) a cellulase originating from a fungus belonging to the genus Aspergillus and a cellulase originating from a fungus belonging to the genus Trichoderma are used.

* * * * *